(12) United States Patent
Schram et al.

(10) Patent No.: US 9,511,019 B2
(45) Date of Patent: Dec. 6, 2016

(54) PHARMACEUTICAL COMPOSITIONS FOR TREATING IBD

(75) Inventors: Hans Schram, Marolles En Brie (FR); Michael Ikechukwu Ugwoke, Amstelveen (NL); Laura Buttafoco, Utrecht (NL)

(73) Assignees: NORDIC PHARMA, Paris (FR); DISPHAR INTERNATIONAL BV, Hengelo (NL)

( * ) Notice: Subject to any disclaimer, the term of this patent is extended or adjusted under 35 U.S.C. 154(b) by 0 days.

(21) Appl. No.: 13/391,825

(22) PCT Filed: Aug. 25, 2010

(86) PCT No.: PCT/IB2010/053812
§ 371 (c)(1),
(2), (4) Date: Feb. 23, 2012

(87) PCT Pub. No.: WO2011/024122
PCT Pub. Date: Mar. 3, 2011

(65) Prior Publication Data
US 2012/0149667 A1    Jun. 14, 2012

(30) Foreign Application Priority Data

Aug. 26, 2009  (EP) .................................... 09290645

(51) Int. Cl.
| | | |
|---|---|---|
| A61K 31/573 | (2006.01) | |
| A61K 9/00 | (2006.01) | |
| A61K 31/60 | (2006.01) | |

(52) U.S. Cl.
CPC ........... *A61K 9/0031* (2013.01); *A61K 31/573* (2013.01); *A61K 31/60* (2013.01); *A61K 9/0095* (2013.01)

(58) Field of Classification Search
CPC .. A61K 9/0031; A61K 9/0095; A61K 31/573; A61K 31/60
See application file for complete search history.

(56) References Cited

U.S. PATENT DOCUMENTS

| | | | | |
|---|---|---|---|---|
| 5,811,388 A | * | 9/1998 | Friend et al. | 424/474 |
| 2006/0127484 A1 | * | 6/2006 | Speirs et al. | 424/489 |

FOREIGN PATENT DOCUMENTS

| | | |
|---|---|---|
| DE | 19849737 | 5/2000 |

OTHER PUBLICATIONS

English Translation of DE 19849737, 2000.*
Declerck D et al: "Pneumopathie Interstitielle Diffuse Iatrogene Liee AU 5-Aminosalycilate" Revue Des Maladies Respiratoires, Paris, FR. vol. 11, Jan. 1, 1994, p. 292/293, XP000901433; ISSN: 0761-8425; abstract p. 292, paragraph 2—col. 2.
Gionchetti P et al: "P155-Efficacy of enemas containing combination of mesalazine and methyl-prednisolone in active distal refractory ulcerative colitis" Journal of Chron'S and Colitis; vol. 3, No. 1; Feb. 1, 2009, p. S72, XP025961565; ISSN: 1873-9946 [retrieved on Feb. 1, 2009].
Gionchetti P et al: "S1052 Efficacy of Enemas Containing Combination of Mesalazine and Methyl-Prednisolone in Active Distal Refractory Ulcerative Colitis" Gastroenterology, Elsevier, Philadelphia, PA, vol. 136, No. 5, May 1, 2009, pp. A-178, XP026111349; ISSN: 0016-5085.
J.M. Rhodes, R. Robinson, I. Beales, S. Pugh, R. Dickinson, M. Dronfield, C.J. Speirs, P. Wilkinson & S.P. Wilkinson: "Clinical trial: oral prednisolone metasulfobenzoate (Predocol) vs. oral prednisolone for active ulcerative colitis" Alimentary Pharmacology & Therapeutics, vol. 27, Feb. 1, 2008, pp. 228-240, SP002564374.
W. Luman, R.S. Grayt, R. Pendek & K. R. Palmer: "Prednisolone metasulphobenzoate foam retention enemas suppress the hypothalarno-pituitary-adrenal axis" Alimenttary Pharmacology & Therapeutics, vol. 8, Apr. 1, 1994, pp. 255-258, SP002564457.

* cited by examiner

*Primary Examiner* — Wu-Cheng Winston Shen
*Assistant Examiner* — Christopher R Stone
(74) *Attorney, Agent, or Firm* — Jerold I. Schneider; Schneider Rothman Intellectual Property Law Group, PLLC

(57) ABSTRACT

A stable and/or synergistic pharmaceutical composition including: a) predinisolone metasulfobenzoate (PMSB) or its acceptable salts, preferably prednisolone metasulfobenzoate sodium and b) 5-ASA, derivatives or pharmaceutically acceptable salts thereof, which is suitable for rectal administration.

8 Claims, No Drawings

PHARMACEUTICAL COMPOSITIONS FOR TREATING IBD

CROSS-REFERENCE TO RELATED APPLICATIONS

This application is the entry into the United States of PCT Application Number PCT/IB2010/053812 filed Aug. 25, 2010, which claims priority to EP09290645.2, filed Aug. 26, 2009, the entirety of each which is hereby incorporated by reference.

FIELD OF THE INVENTION

The present invention relates to a new pharmaceutical combination of active ingredients having improved properties and/or synergistic therapeutical action for the treatment of inflammatory bowel diseases.

BACKGROUND OF THE INVENTION

Inflammatory Bowel Disease (IBD) is the general name for diseases that cause inflammation in the small intestine and colon and usually relates to three gastrointestinal disorders of unknown etiology, namely, ulcerative colitis, Crohn's disease, and indeterminate colitis. They have many symptoms in common with irritable bowel syndrome, including abdominal pain, chronic diarrhea, weight loss, and cramping which makes the definitive diagnosis extremely difficult. Ulcerative colitis, also referred to as UC, is the most common inflammatory bowel disease and affects various portions of the gastrointestinal tract (GI), particularly the lower GI tract, and more particularly the colon and/or rectum. Almost without exception, UC starts involving the rectum before it spreads proximately to contiguous portions or to the entire colon. The disease activity is usually intermittent, with relapses and periods of quiescence. In mild UC, the colonic mucosa appears hyperaemic and granular, wherein in more severe cases, tiny punctuate ulcers are present and the mucosa is characteristically friable and may bleed spontaneously. Crohn's disease predominates in the small and the large intestine. Diseased patients usually have deeper inflammations in the most distal part of the small intestine and the first part of the large intestine (ileocaecal region), but the inflammation can be located in any part of the gastrointestinal tract.

It is now well documented that such diseases are also usually associated with an increased risk of subsequent gastrointestinal cancer, especially colorectal cancer, and eventhough the mechanisms are not yet proven, pathways which could lead to subsequent transformation, heightened proliferation and malignant invasion occurring during multiple acute inflammatory episodes, are disclosed in patent application WO 95/18622. In this context, it is appropriate to seek for efficient methods of treatment of IBD.

Up to the present days, existing drug therapies cannot cure IBD, but tend to reduce as much as possible the intestinal inflammation. Existing treatments basically depend on the seriousness of the illness, which might sometimes lead to surgical removal of the diseased colon. For ulcerative colitis, most people are treated for life with medication containing aminosalicylates, such as 5-aminosalicylic acid (5-ASA), or 4-aminosalicylic acid (4-ASA) to help control the inflammation. 5-ASA is chemically related to aspirin and has the same analgesic, antipyretic and anti-inflammatory properties. It is part of the Non Steroidal Anti Inflammatory Drugs (NSAID) and has been used for years in the treatment of Crohn's disease and especially for Ulcerative Colitis where it markedly reduces the chance of a flare up. Different suitable derivatives containing aminosalicylates have already demonstrated their efficacy and are presently on the market. For instance, sulfasalazine contains 5-ASA and sulfapyridine which role is to help carrying the anti inflammatory drug to the intestine.

Increased leukocyte migration, abnormal cytokine production, increased production of arachidonic acid metabolites (particularly leukotriene $B_4$), and increased free radical formation in the inflamed intestinal tissue are all present in patients with Inflammatory Bowel Diseases. Oral or local administration of 5-ASA allows the drug to act locally on the diseased area as it is absorbed by colonic and intestinal epithelial cells where its effectiveness depends on the mucosal concentration, by inhibiting leukocyte chemotaxis, decreasing cytokine and leukotriene production, and scavenging free radicals. A description of the mechanisms of action as well as a review of effective dosages are disclosed in Campieri, et al., "*Optimum dosage of 5-aminosalicylic acid as rectal enemas in patients with active ulcerative colitis*", Gut, 1991(8) pp 929-931, and Wallace J. L., et al., "*Inhibition of leukotriene synthesis markedly accelerates healing in a rat model of inflammatory bowel disease*", Gastroenterology, 1989. 96(1): pp 29-36.

Prednisolone, ((11β)-11,17,21-trihydroxypregna-1,4-diene-3,20-dione), is a synthetic corticosteroid that is of significant importance in the treatment of inflammatory diseases. It is disclosed in U.S. Pat. No. 3,134,718 and in general, is known to be efficient in the treatment of inflammatory and immune diseases. Indeed, the sodium phosphate salt of prednisolone is known to be used to treat a vast array of conditions including: allergic states, dermatologic diseases, endocrine disorders, neoplastic disorders, and rheumatic disorders while the acetate salt is known for use in ophthalmic preparations. Products are now currently available on the market in oral dosage forms such as in Cortancyl® (prednisolone acetate) or Medrol® (methylprednisolone), as well as in enemas such as in Predsol® (prednisolone sodium phosphate).

The prednisolone metasulfobenzoate (PMSB) is also already known. It is currently commercially available in its sodium salt form such as in the Solupred®, or Predocol® products and several controlled release oral forms comprising PMSB are disclosed, as in WO 2003/68196 for example.

In addition, further improvements in the research of new IBD drug treatments have led to the development of new steroid drugs such as tixocortol pivalate, fluticasone propionate, beclomathasone dipropionate and budesonide, which appeared to be a highly potent topical glucocorticosteroid. Specific combinations of these drugs are known, such as in WO 00/24388 which discloses examples of combinations of budesonide with 5-ASA that are useful for the treatment of IBD.

However, whereas improvements in the state of the art are usually directed to galenic considerations in order to locate the delivery of the active ingredients at the specific sites of adsorption, the efficacy of the existing forms remain however limited by the physical properties and therapeutical potency of the active ingredient that are used. Because PMSB is easily degraded, there is a need to provide improved compositions that would provide a higher therapeutical utility.

It has been surprisingly found that PMSB or its pharmaceutically acceptable salts thereof in combination with 5-ASA, derivatives or pharmaceutically acceptable salts thereof resulted in highly stable formulations that were useful in the treatment of IBD. Also, it has been surprisingly found that the combination of these two active ingredients resulted in composition having synergic effects.

SUMMARY OF THE INVENTION

According to a first aspect, the invention is directed to a pharmaceutical composition comprising:
a. prednisolone metasulfobenzoate or its pharmaceutically acceptable salts (PMSB), preferably prednisolone metasulfobenzoate sodium, and
b. 5-ASA, derivatives or pharmaceutically acceptable salts thereof.

According to one embodiment, the pharmaceutical composition of the invention is in the form of a powder, a granulate or a suspension, preferably for use in a tablet, an enema, a foam, an oral dosage form, an immediate release form, a delayed release form or a sustained release form.

According to another embodiment, the pharmaceutical composition of the invention is suitable for rectal administration.

According to another embodiment, the pharmaceutical composition of the invention comprises a combination of PMSB and 5-ASA, derivatives or pharmaceutically acceptable salts thereof in a solid pharmaceutical formulation, preferably for reconstitution into an enema.

According to another embodiment, the pharmaceutical composition of the invention is substantially free of buffer.

According to another embodiment, the pharmaceutical composition of the invention further comprises a viscosity enhancer, preferably in an amount of from about 0.05 to 2.5% by weight, more preferably in an amount of from about 1 to 1.75% by weight.

According to another embodiment, the viscosity enhancer is selected from acacia gum, ceratonia gum, agar gum, xanthan gum, guar gum, dextrin, xylitol, erythritol, tragacanth, fructose, sorbic acid, poloxamer, carragenan, edetic acid, cellulose derivatives, carboxymethylcellulose or hydroxypropylmethylcellulose and is preferably guar gum.

According to another aspect, the invention is directed to a composition for reconstitution into an enema, comprising:
(i) Prednisolone metasulfobenzoate (PMSB) and its pharmaceutically acceptable salts, preferably prednisolone metasulfobenzoate sodium and 5-ASA, derivatives or pharmaceutically acceptable salts thereof in granules,
(ii) a bottle,
for simultaneous, separate or sequential therapeutical use as a combined preparation.

According to one embodiment, the component (ii) is empty, filled with water or filled with the granules (i).

According to another embodiment, the composition of the invention comprises a synergistic amount of component a) and b).

According to another embodiment, the weight ratio a:b is from about 1:1 to about 1:200, preferably of from about 1:20 to about 1:150.

According to another embodiment, the composition of the invention comprises a total amount of from about 10 to 50 mg of component a), preferably 20 to 40 mg, and more preferably about 31.4 mg. and a total amount of from about 0.5 to 5 grams of component b), preferably of from about 1 to 4 grams, and more preferably of about 1.0 grams.

According to another embodiment, the composition of the invention comprises prednisolone metasulfobenzoate sodium in an amount of 31.4 mg and 5-ASA in an amount of 1.0 gram.

According to another embodiment, the composition of the invention is for the treatment of Inflammatory Bowel Diseases, especially Ulcerative Colitis or Crohn's disease.

According to another aspect, the present invention is directed to prednisolone metasulfobenzoate or its pharmaceutically acceptable salts, preferably prednisolone metasulfobenzoate sodium for its simultaneous, separate or sequential therapeutical use with 5-ASA, derivatives or pharmaceutical acceptable salts thereof.

According to another aspect, the present invention is directed to the use of prednisolone metasulfobenzoate or its pharmaceutically acceptable salts, preferably prednisolone metasulfobenzoate sodium in combination with 5-ASA, derivatives or pharmaceutically acceptable salts thereof for the preparation of stable powder, granules, enema, suspension, foam, oral dosage form, immediate release form, delayed release form or sustained release form, preferably granules to be reconstituted as an enema.

According to another aspect, the present invention is directed to a process for preparing a composition according to the present invention, comprising the step of associating a) prednisolone metasulfobenzoate or its pharmaceutically acceptable salts, preferably prednisolone metasulfobenzoate sodium with b) 5-ASA, derivatives or pharmaceutically acceptable salts thereof, optionally further step of conditioning into a powder, granules, an enema, a foam, an oral dosage form, an immediate release form, a delayed release form, or a sustained release form.

According to one embodiment, the process of the invention comprises the step of reconstituting an enema by adding water to granulates comprising the components a) and b).

DETAILED DESCRIPTION OF THE INVENTION

The present invention relies on the surprising finding that the association of a) prednisolone metasulfobenzoate (PMSB) and b) 5-aminosalicylic acid (5-ASA), derivatives or pharmaceutically acceptable salts thereof provided compositions that were more stable in water in comparison to compositions of the prior art comprising a) PMSB alone. The present invention is particularly advantageous in the treatment of inflammatory bowel diseases such as ulcerative colitis or Crohn's disease.

Because drugs for the treatment of IBD need to be administered to the wounded areas, it may be necessary to administer the compounds locally to the rectum and lower intestine i.e. by using enemas or foams. While PMSB and 5-ASA that are usually formulated separately in an aqueous medium become usually rapidly degraded, this results in a decrease of the therapeutical potency of the product. Thus, it is now possible by using a combination of a) and b) to provide dosage forms that remain unaltered, either for storage purposes or an increased stability of the compositions after administration once introduced into the body.

Similarly, oral dosage forms travel through the gastrointestinal tract via the stomach and are usually formulated so that the drugs are released after the stomach. This is to avoid the ulcerative effect of 5-ASA but also to direct the delivery of the drugs to the wounded portions of the intestine. Thus, it is advantageous to use a composition that remains stable once in contact with the aqueous gastric juice.

More generally, the compositions of the present invention are useful for any dosage form that requires the addition of water during formulation, such as a conventional granulation for example.

According to one embodiment, the compositions of the present invention may be substantially free of buffer. While solutions of the prior art usually require a buffer to ensure the stability of the composition over the time of administration, it was surprisingly observed that solutions of the present invention comprising PMSB with 5-ASA, that were for example reconstituted from granules comprising the two active ingredients, were stable even at a pH below 4.5. The use of buffers such as acetate buffer (pH of 4.5-4.8) is thus no longer required. Furthermore, it was also observed that the use of these buffers could in fact enhance the degradation of the active ingredients. Stability tests are provided in the examples. The term "substantially free" implies that the compositions within the scope of the invention may be as free of buffer as it is practically and realistically feasible.

The first component a) is the prednisolone metasulfobenzoate or its pharmaceutically acceptable salts. In the present application, the term PMSB refers to prednisolone metasulfobenzoate as well as to any of its pharmaceutically acceptable salts. For example, prednisolone metasulfobenzoate may advantageously be present as sodium salt.

Typically, 31.4 mg of PMSB sodium salt corresponds to about 20 mg of prednisolone free base. Thus, the compositions according to the present invention comprises PMSB or any pharmaceutically acceptable salts in an amount corresponding to about 6 to 32 mg, preferably about 13 to 26 mg and more preferably to about 20 mg of prednisolone free base.

We refer in the present application to weights based on the PMBS for the amounts and ratios.

The 5-ASA component b) may be present in the form of its salts or metal complexes which are also encompassed into the mixtures of the present invention.

Salts are produced by reaction with acids, for examples hydrohalic acids such as hydrofluoric acid, hydrochloric acid, hydrobromic acid, hydroiodic acid, sulfuric acid, phosphoric acid, nitric acid, or organic acids such as acetic acid, benzoic acid, cinnamic acid, oxalic acid, formic acid, benzenesulfonic acid, p-toluenesulfonic acid, methanesulfonic acid, salicylic acid, p-aminosalicylic acid and 1,2 naphthalenedisulfonic acid.

Metal complexers are prepared from the basic organic molecule and an inorganic or organic metal salt, for example the halides, nitrates, sulfates, phosphates, acetates, trfluoroacetates, trichloroacetates, propionates, tartrates, sulfonates, salicylates, and benzoates of metal of the second main group, such as calcium and magnesium, and of the third and fourth main groups, such as aluminium, tin or lead, and of the first to eight sub-group, such as chromium, manganese, iron, cobalt, nickel, copper and zinc.

Derivatives of the active ingredients b) may also be used. For example any drug which contains 5-ASA may be incorporated within the present invention, such as by way of non limiting examples, ipsalazine, balsalazine, sulfalazine, salazopyrine, salazosulfapyridine, olsalazine or mesalazine, oxidized derivative, prodrugs, etc., or mixture thereof. Typically, pure 5-aminosalicylic acid and metasulfobenzoate sodium salt of prednisolone (PMSB) are used, to which other active ingredients such as therapeutically effective drugs can be added.

The present invention further relies on the surprising finding that composition comprising a) prednisolone metasulfobenzoate (PMSB) or one of its pharmaceutically acceptable salts and b) 5-amino salicylic acid (5-ASA) provides a synergistic therapeutical action. The synergistic effect of the composition is apparent from the fact that the therapeutical effect of the composition of component a) and b) is greater than that any of the active ingredients alone or of the additive activity that would be predicted for the combination based on the activities of the individual components. This is demonstrated in example 1.

The synergy is also observed for prednisolone or any type of prednisolone derivatives or pharmaceutically acceptable salts thereof that is different from PMSB when associated in combination with the component b), derivatives or pharmaceutically acceptable salts thereof. Examples of prednisolone derivatives or pharmaceutically acceptable salts are methylprednisolone, methylprednisolone acetate, methylprednisolone sodium succinate, prednisolone acetate or prednisolone sodium phosphate.

Typically, an appropriate ratio (by weight) of compounds a):b) is such that a synergistic therapeutical action occurs. The synergy is particularly observed for example for a ratio of from about 1:1 to about 1:200, preferably of from about 1:20 to about 1:150.

For example, the components may be provided in a ratio of from about 1:1 to about 1:200, of about 1:20 to about 1:150 or of about 1:20 to about 1:50 or of about 1:100 to about 1:150.

The synergistic composition according to the present invention may be, for instance in the form of a powder, a granulate, an enema, a tablet, an oral dosage form, an immediate release form, a sustained form or a foam and depend entirely on the type of administration that is chosen. Typically, foams, suspensions and enemas can be selected for local application to the colon, while tablets are adapted for oral administration.

According to another embodiment of the invention, the components a) and b) represent a synergistic preparation and are used either simultaneously, separately or sequentially for the treatment of inflammatory bowel diseases such as ulcerative colitis or Crohn's disease. For instance, a synergistic effect can be obtained by the intake of a tablet of PMSB together with the administration of a mesalazine enema, when used in the appropriate proportions.

Once the components are provided, they may be taken either simultaneously, separately, or sequentially to obtain the synergistic effect. For example, a combination tablet comprising 5-ASA and PMSB may be taken, or a sustained release prednisolone tablet may be taken prior to the administration of a 5-ASA enema.

The pharmaceutical compositions of the present invention may also contain any pharmaceutically acceptable excipient or combination thereof. Conventional pharmaceutical excipients include those which function in a dosage form, for example, as a viscosity enhancer, lubricant, glidant, diluent, binder, disintegrant, carrier, colorant, preservative, osmotic agents or coating material.

Examples of pharmaceutically acceptable excipients include, but are not limited to, lactose, dextrates, dextrin, dextrose, mannitol, dicalcium phosphate, xylitol, sugar, saccharose, corn starch, hydrolyzed starch (malto-dextrine), modified corn starch, maize starch, dried starch, sodium starch glycolate, mannitol, sorbitol, silicon dioxide, microcrystalline cellulose, croscarmello se sodium, polyvinylpyrrolidone, polyvinylalcohol, hydroxypropylcellulose, hydroxymethylcellulose, hydroxypropylmethylcellulose, alkylcellulose such as methylcellulose or ethylcellulose, gelatin, cross-linked polyvinylpyrrolidone (PVP), sodium carboxymethyl starch, magnesium stearate, sodium stearyl fumarate, polyethylene glycol, stearic acid, hydrogenated vegetable oil, glyceyl behenate and talc, colloidal silica, tribasic calcium phosphate, and mixtures thereof. Suitable osmotic agents may include sodium chloride and dimethyl sulfone.

Viscosity enhancing agents advantageously come into the composition of enemas. Because this particular type of dosage form is intended for a local use, viscosity enhancers provide convenient gelling properties to the suspension that is administered so that it remains into the rectum or upper colon. Examples of such excipients include for example gums, such as acacia gum, ceratonia gum, agar gum, xanthan gum, guar gum, dextrin, xylitol, erythritol, tragacanth, fructose, sorbic acid, poloxamer, carragenan, edetic acid or cellulose derivatives such as carboxymethylcellulose or hydroxypropylmethylcellulose. Guar gum is particularly advantageous. According to another preferred embodiment, the particle size of guar gum is of less than 74 µm for at least 75% of the guar gum particles.

The type and amount of viscosity enhancer may be chosen in a way that prevents settling of the powder or granulate particles after reconstitution when preparing an enema. In order to obtain an enema in the form of a viscous suspension, a concentration of 1 to 1.75% by weight of viscosity enhancer may be used for example. Alternatively, in order to prepare an enema in the form of a gel, for example a concentration of 2% viscosity enhancer may be used.

Tablet dosage forms may contain for example, as excipients, any pharmaceutically acceptable lubricant, binder, disintegrant, diluent, carrier, any preservative or combination thereof.

For example, foam and enema forms may further contain preservatives, in order to inhibit the growth of microorganism.

Foams may contain emulsifiers to improve the dissolution of gaseous propellants, thickeners in order to increase the stability of the emulsion/suspension, foam enhancers, mucoadhesive or buffering agents, and any other additive that is available to the skilled man.

Further excipients are disclosed in "Handbook of Pharmaceutical excipients", $2^{nd}$ Ed., 1994, American Pharmaceutical Association, Washington, ISBN 0 91730 66 8, by Wade A., Weller P J.

Another aim is to provide methods for preparing the compositions and kits of the invention. Such techniques are those that are available to the man skilled in the art.

One process typically consists in associating the components a) and b) in the appropriate amount.

In case where kit of parts are considered, the components a) and b) may be associated in such way that they will be sold together but maintained in separate containers with written instructions to the patient. Instructions may consist in a protocol for a continuous, sequential or separate administration of components a) and b). Instructions may also consist in a protocol for mixing the two separate components into a final dosage form to be administered. Thus, within the scope of the invention, each of the components a) and b) may be independently under the form of a powder, an enema, a suspension, a foam, an oral dosage form, an immediate release form, a tablet, or a sustained release form.

According to another embodiment, the components a) and b) will be formulated together, and associated with a bottle and written instructions to the patients to reconstitute an enema that is ready to use.

For example, one particular kit of part or composition within the scope of the invention will be in the form of a same commercial product provided with a first container of granules comprising PMSB and 5-ASA, with a second container such as an empty bottle and a written notice to the patient that teaches how to mix the granules into an aqueous medium in order to reconstitute an enema. Alternatively, the bottle may be already filled with water and be associated with a notice that provides a protocol to the patient to reconstitute an enema by adding the granules into the bottle filled with water. According to another alternative, the bottle may be filled with the granules comprising components a) and b) and be associated with a notice that provides a protocol to the patient to reconstitute an enema by adding water into the bottle already filled with the granules.

In order to prepare the compositions of the invention, once the components a) and b) are associated, the typical process may optionally comprise the further step of conditioning the resulting association into the form of a powder, a granulate, an enema, a foam, a tablet, an oral dosage form, an immediate release form, or a sustained release form. For example, an enema within the scope of the invention may be reconstituted from granulates comprising PMSB and 5-ASA that are added to water.

Enemas may be prepared by conventional techniques from the association of components a) and b), independently in the form of granules or powders, into a suspension. For example, enemas of the present inventions may result from the mixing of an enema comprising component a) and another enema comprising component b), or from suspending a mixture of components a) and b) in a granulate or powder form into an aqueous media. Enemas within the scope of the invention may also be reconstituted from granulates comprising PMSB and 5-ASA when added to water.

Tablets may be prepared from the association of granules of component a) and b) into the appropriate amounts and the further compression of the resulting mixture with extragranular excipients, into an immediate or sustained release tablet.

The processing foams may comprise a first step comprising the mixing of components a) and b) optionally with other excipients that are appropriate for suitable foam compositions. The resulting mixture may then be pressurized.

The novel compositions or kits may be administered to patients afflicted with IBD such as ulcerative colitis or Crohn's disease. Appropriate dosage should be based upon the severity of the disease and the dosage form that is considered. For example if the compositions of the invention are to be administered as a sustained release dosage form having effects over prolonged periods of time, the amount of active ingredients will be accordingly loaded.

The following examples are merely illustrative of several embodiments of the present invention and should not be construed as limiting the scope of the invention.

EXAMPLES

Example 1

Induction of TNBS Colitis and Evaluation of Macroscopic Lesions in the Colitis after Administration of 5-ASA, PMSB, and Synergistic Combination of 5-ASA and PMSB.

Animal experiments were performed in accredited establishments according to governmental guidelines. Animals were housed five per cage and had free access to standard mouse chow and tap water.

Colitis induction was conducted on C57bl6 mice aged of 6 weeks old. They were anesthetized for 90-120 minutes before they received intrarectal administration of TNBS (trinitrobenzene sulphonic acid) (40 µl, 150 mg/kg) dissolved in a 1:1 mixture of 0.9% NaCl with 100% ethanol. Control mice received a 1:1 mixture of 0.9% NaCl with 100% ethanol or a saline solution using the same technique. Animals were sacrificed 4 days after TNBS administration. The anti-inflammatory effect of 5-ASA and steroid was evaluated by daily administration of these compounds by intrarectal route in a final volume of 50 μl, starting 3 days before the colitis induction and during all the experiment (4 days after colitis induction). Dosage amount of 5-ASA was 0.5 mg (50 μl of 1 g/100 ml stock), 65 mM and the dosage amount of PMSB was 2.34 mg/kg/day.

Given the fact that mice may be administered higher dosages of prednisolone or derivatives thereof than human patients, typically amounts that are five times higher, the present example clearly illustrates the synergistic combination according to the present invention.

The macroscopic assessments of colitis were performed blindly by two investigators. The colon of each mouse was examined under a dissecting microscope (magnification, ×5), to evaluate the macroscopic lesions according to the Wallace criteria. The score rates macroscopic lesions on a scale of from 0 to 10 based on the features reflecting inflammation, such as hyperaemia, thickening of the bowel, and extent of ulceration. The Wallace scale is defined as follows. A score of 0 represents an absence of inflammation, a score of 1, a hyperaemia without ulcerations, a score of 2 a hyperaemia with a thickening of the mucosa without ulcerations, a score of 3, one ulceration without thickening of the colonic wall, a score of 4, two or more ulcerative or inflammatory sites, a score of 5, two or more ulcerative and inflammatory sites with an extent of more than 1 cm, and for a score of from 6 to 10, an ulcerative or inflammatory site of growing size of from 2 to 6 cm.

The results show that a significant decrease in the intensity of lesions is observed in the colitic mice treated by combination of PMSB with 5-ASA that provided synergistic effects. Indeed, the Wallace scores are 1.83 for the group treated only with PMSB (P group), 1.25 for the group treated with 5-ASA (A group), and 0.5 for the group treated with the synergistic combination of both products (A+P group). The control group of untreated mice only scored 3.4.

These results were converted into action percentage, in comparison to the Wallace score obtained with mice that where not treated (control group). A score of Wallace of 3.4 thus indicates an action of 0% and a score of 0, (no lesion) indicates 100% action. According to this experiment, the A group showed an action of 63%, the P group of 46% and the A+P group of 85%. The action that the active ingredients would be expected to have in combination was calculated according to the Colby formula, and a comparison in the actions was then observed.

The Colby formula is $E=X+Y-(X \times Y)/100$, wherein E is the expected degree of action, expressed in %, when the active ingredients 5-ASA and prednisolone PMSB are used in combination. X is the degree of action, expressed in % of the untreated control, when active ingredient 5-ASA is used by itself. It is the degree of action converted from the Wallace score obtained for the A group. Y is the degree of action, expressed in % of the untreated control, when active ingredient PMSB is used by itself. It is the degree of action converted from the Wallace score obtained for the P group.

In the instant case, the expected action is $63+46-(63*46/100)=80\%$ for the combination of 5-ASA with PMSB, and this expected value is far below the value that was measured further to the treatment with the synergistic combination.

Example 2

The compatibility of mesalazine and sodium prednisolone metasulfobenzoate (PMSB) was evaluated. The following mixtures were tested:
1. A dry powder blend of PMSB and 5-ASA;
2. PMSB dissolved in 100 ml water;
3. A blend of both PMSB and 5-ASA in 100 ml water and
4. A blend of both PMSB and 5-ASA in 100 ml water using an acetate buffer.

The stability of the formulations was evaluated at either 25° C./60% RH or 40° C./75% RH as long as degradation was observed, but in all cases for a maximum of 1 or 3 months. The stability of PMSB alone in water was instead evaluated at ambient conditions for one month. At several intervals (2 days, 7 days, 1 or 3 months) the test samples were analysed by measuring the amount of PMSB and its related substances present. The measurements were performed by means of chromatography, according to European Pharmacopoeia standards.

The product specification was set at 31.4 mg±5% PMSB and hence all test samples with a PMSB content of less than 29.8 mg are regarded as unstable. Additionally, the product specifications were set to contain less than 2% impurities. Measurements were then interrupted when either one of the other parameter was out the required specifications. The results obtained are indicated in table I.

TABLE I

PMSB content in the samples (in mg) and/or total impurities (in %)

| Formulation | T0 | Amount of PMSB in mg | | | | Total impurities T |
|---|---|---|---|---|---|---|
| | | T (2 days) | T (7 days) | T (1 month) | T (3 months) | |
| PMSB & 5-ASA as dry powder (40° C./75% RH) | 33.3 ± 0.3 | ND | ND | 31.2 ± 0.4 | 33.5 ± 0.2 | 0.5% (1 month) 0.6% (3 months) |
| PMSB Na water (ambient conditions) | 30.8 ± 0.1 | ND | ND | ND | ND | 19.5% (1 month) |
| Powder blend PMSB & 5-ASA in water (25° C./60% RH) | 32.2 ± 0.2 | ND | 29.9 | 30.8 ± 0.1 | | 1.1% (1 month) |
| Powder blend PMSB & 5-ASA in water (40° C./75% RH) | 32.2 ± 0.2 | 31.3 ± 0.1 | 29.4 ± 0.1 | 28.8 ± 0.2 | ND | 1% (7 days) 4.3% (1 month) |
| Powder blend PMSB & 5-ASA in acetate buffer (25° C./60% RH) | 30.8 ± 0.2 | ND | 28.8 | ND | ND | 2.1% (immediately after mixing) |
| Powder blend PMSB & 5-ASA in acetate buffer (40° C./75% RH) | 30.8 ± 0.1 | 29.2 ± 0.1 | 27.5 ± 0 | ND | ND | 2.1% (immediately after mixing) |

The results of the stability study clearly demonstrate that a dry powder blend of both API's is stable for at least 3 months, and that formulation of PMSB in water in association with 5-ASA provides a highly improved stability in comparison to formulations of PMSB in water.

Example 3

A formulation according to the invention may be prepared by granulating 1% w/w PMSB together with 31% w/w of 5-ASA (1 gram of 5-ASA), 2% w/w crospovidone (disintegrating agent), 38% w/w guar gum (viscosity enhancer) and 28% w/w NaCl (isotonic agent). The amounts are based on the total weight of the final granulates. Granules of the present example are appropriate to be added to 100 ml water to reconstitute an enema that is ready to use.

The invention claimed is:

1. A pharmaceutical composition comprising an aqueous solution of:
   (a) 20 to 40 mg/100 mL of prednisolone metasulfobenzoate sodium (PMSB); and
   (b) 1 to 4 g/100 mL of mesalazine (5-ASA);
wherein said solution does not comprise a buffer and the PMSB is decomposed by no more than 3% when maintained for seven days at 40 degrees Celsius and 75% relative humidity.

2. The pharmaceutical composition according to claim 1, in the form selected from the group consisting of an enema, an oral dosage for immediate release, and an oral dosage for sustained release.

3. The pharmaceutical composition according to claim 1, further comprising a viscosity enhancer, in an amount of from about 0.05 to 2.5% by weight.

4. The composition according to claim 1, further comprising a viscosity enhancer, in an amount of from about 1 to 1.75% by weight.

5. The pharmaceutical composition according to claim 3, wherein the viscosity enhancer is selected from acacia gum, ceratonia gum, agar gum, xanthan gum, guar gum, dextrin, xylitol, erythritol, tragacanth, fructose, sorbic acid, poloxamer, carrageenan, edetic acid, cellulose derivatives, carboxymethylcellulose or hydroxypropylmethylcellulose.

6. A method for the treatment of inflammatory bowel disease (IBD) comprising the step of administering a pharmaceutically effective amount of the pharmaceutical composition of claim 1.

7. The method according to claim 6, wherein the IBD is selected from the group consisting of Ulcerative Colitis and Crohn's Disease.

8. The method according to claim 6, wherein the pharmaceutical composition is administered in a form selected from the group consisting of an oral dosage and an enema.

* * * * *